United States Patent [19]
Kim et al.

[11] Patent Number: 6,123,963
[45] Date of Patent: Sep. 26, 2000

[54] USE OF WATER-SOLUBLE OR WATER-DISPERSIBLE POLYURETHANES AS COATINGS OR BINDERS FOR PHARMACEUTICAL PRESENTATIONS

[75] Inventors: Son Nguyen Kim, Hemsbach; Axel Sanner, Frankenthal; Karl Kolter, Limburgerhof, all of Germany

[73] Assignee: BASF Aktiengesellschaft, Ludwigshafen, Germany

[21] Appl. No.: 09/168,098

[22] Filed: Oct. 8, 1998

[30] Foreign Application Priority Data

Oct. 9, 1997 [DE] Germany .......................... 197 44 473

[51] Int. Cl.⁷ ................................ A61K 9/32; A61K 9/58
[52] U.S. Cl. .......................... 424/482; 424/462; 424/463; 424/459; 424/474; 424/475; 424/490; 424/497; 424/465
[58] Field of Search ..................... 424/475, 459, 424/462, 482, 497, 463, 474, 490, 465

[56] References Cited

U.S. PATENT DOCUMENTS 4,743,673  5/1988  Johnston et al. .......................... 528/60
4,789,720  12/1988  Teffenhart .................................. 528/76

FOREIGN PATENT DOCUMENTS

| | | |
|---|---|---|
| 2172987 | 4/1995 | Canada . |
| 315 19 923 | 7/1982 | Germany . |
| 42 25 045 | 2/1994 | Germany . |
| 42 41 118 | 6/1994 | Germany . |
| 43 33 238 | 4/1995 | Germany . |
| 195 41 326 | 5/1997 | Germany . |
| 2 090 264 | 7/1982 | United Kingdom . |

*Primary Examiner*—James M. Spear
*Attorney, Agent, or Firm*—Keil & Weinkauf

[57] ABSTRACT

The use of water-soluble or water-dispersible polyurethanes which consists of
a) 0.1–30% by weight of at least one polyol,
b) 20–45% by weight of at least one polyetherpolyol,
c) 10–45% by weight of at least one diamine comprising an ionic group,
d) 30–50% by weight of at least one polyisocyanate with or without
e) further additives as coatings or binders for pharmaceutical presentations.

11 Claims, No Drawings

USE OF WATER-SOLUBLE OR WATER-DISPERSIBLE POLYURETHANES AS COATINGS OR BINDERS FOR PHARMACEUTICAL PRESENTATIONS

The present invention relates to the use of water-soluble or water-dispersible polyurethanes as coatings or binders for pharmaceutical presentations.

Solid pharmaceutical presentations such as tablets, capsules, pellets, granules, crystals etc. are coated, ie. provided with a film coating, for a wide variety of reasons. Thus, for example, an unpleasant odor or taste can be masked, and the swallowability can be improved. The stability of the active ingredients may be increased by the coating since less water vapor and oxygen reach the interior of the tablet. The presentations have a better appearance and can be distinguished better by incorporating dyes. Furthermore, in particular, the rate of release of the active ingredient can be adjusted by the film coating.

A distinction is generally made between instant release forms and slow release forms.

In the case of instant release forms, the disintegration of the tablet and the release of the active ingredient from the presentation should, where possible, not be influenced by the coating, for which reason the film coating must dissolve rapidly in gastric fluid. In addition, it must have good film properties. The tensile strength and the ultimate elongation should be high, so that the film coating withstands mechanical effects occurring during pharmaceutical processing—especially packaging—and during transport and storage.

A product which is frequently employed for coating instant release tablets is hydroxypropylmethylcellulose (HPMC). Hydroxypropylmethylcellulose shows a steep increase in viscosity as the concentration increases in aqueous solution.

Since the solution of film former must be finely atomized for coating tablets, and the droplets which are formed must thoroughly wet the surface of the tablets, as well as spread well, the viscosity must not exceed a certain limit (from 150 to 250 mpas) which depends on the type of spray nozzle and of apparatus. It is therefore possible in the case of HPMC to employ only relatively low concentrations of film former.

The recommended concentration for Pharmacoat® 606 (supplied by Shin-etsu) in the literature is 5–7% by weight (Pharmaceutical Coating Technology, edited by Graham Cole, Taylor and Francis Ltd. 1995 and, manufacturers' technical data sheets). These low spray concentrations result in relatively long processing times and thus high costs.

In addition, hydroxypropylmethylcellulose has further disadvantages, inter alia in the wetting characteristics, in the adhesiveness to the tablet surface, in the pigment-binding capacity, in the mechanical properties of the films, in the hygroscopicity, and in the permeability to water vapor and oxygen and in the difference in disintegration times between film-coated tablets and core.

It is an object of the present invention to provide water-soluble or water-dispersible polyurethanes as coatings or binders for pharmaceutical presentations which do not have the abovementioned disadvantages.

We have found that this object is achieved by the use of water-soluble or water-dispersible polyurethanes consisting of a) 0.1–30% by weight of at least one polyol,
b) 20–45% by weight of at least one polyetherpolyol,
c) 10–45% by weight of at least one diamine comprising an ionic group,
d) 30–50% by weight of at least one polyisocyanate with or without e) further additives.

Polyurethanes, and polyesters as well as poly(ester-urethanes) have already been disclosed as auxiliaries in pharmaceutical formulations.

Thus, DE-A-42 25 045 describes the use of water-soluble or water-dispersible polyurethanes consisting of at least one compound which comprises two or more active hydrogen atoms per molecule, of one diisocyanate and of a diol comprising acidic or salt groups. The diols comprising carboxylate groups have the disadvantage that they make the polymer insoluble in gastric fluid.

The polyurethanes described in DE-A-42 41 118 and consisting of polyesterdiols/diols/tert-amine-containing diols or diamines/diisocyanates are labile to hydrolysis in the acidic pH range and tend to form tacky films.

DE-A-43 33 238 claims pyrrolidone group-containing polyesters and polyamides as constituent of film coatings in pharmaceutical formulations. The polyesters described herein are likewise too labile to hydrolysis under gastric acid conditions. Said polyamides have the disadvantage that they are too viscous and too tacky and therefore do not have the properties required of film formers.

DE-A-31 51 923 describes crosslinked polyetherurethanes which can be employed as tabletting auxiliaries. However, in order to achieve the required solubility in water of the crosslinked polyetherurethanes, the polyether content must be chosen to be so high that the polymer is too tacky.

U.S. Pat. Nos. 4,743,673; 3,388,159 and 4,789,720 describe polyurethanes which either are insoluble in water or form undesirably tacky films.

The polyurethanes according to the invention and their structural components a) to d) can be described in detail as follows.

The polyols used as component a) are low molecular weight polyols, in particular diols comprising 2 to 10 carbon atoms and having an MW≦500 g/mol. Suitable and preferred representatives of this class are ethylene glycol, 1,2-propylene glycol and 1,3-propylene glycol, 1,4-butanediol, 1,3-butanediol, 1,4-butenediol, 1,4-butynediol, 1,5-pentanediol, 1,6-hexanediol, 1,8-octanediol, neopentyl glycol, cyclohexanedimethanol (1,4-bishydroxymethylcyclohexane), 2-methyl-1,3-propanediol, also diethylene glycol, triethylene glycol, tetraethylene glycol, dipropylene glycol and dibutylene glycol. Triols such as glycerol are also suitable.

Particularly preferred diols are 1,6-hexanediol and 1,4-bishydroxymethylcyclohexane.

The amounts of component a) in the polyurethane according to the invention are in the range from 0.1 to 30% by weight, preferably in the range from 0.3 to 20% by weight, particularly preferably in the range from 0.5 to 15% by weight.

Components b) are polyetherpolyols, in particular polyetherdiols, having a molecular weight of from 300 to 6000 g/mol, preferably 500 to 4000 g/mol, particularly preferably 500 to 2000 g/mol.

The polyetherdiols which can be employed can be obtained in particular by polymerizing ethylene oxide, propylene oxide, butylene oxide, tetrahydrofuran, styrene oxide or epichlorohydrin with itself, e.g., in the presence of $BF_3$, or by addition of these compounds, as mixture or successively, onto starter components with reactive hydrogen atoms, such as alcohols or amines, e.g. water, ethylene glycol, 1,3-propylene glycol or 1,2-propylene glycol, 4,4'-dihydroxydiphenylpropane or aniline.

Preferred polyetherdiols are polytetrahydrofuran with a molecular weight of from 500 to 2000 g/mol, and polyethylene glycol and polypropylene glycol with a molecular weight of from 500 to 2000 g/mol.

It is also possible to replace up to 30 mol % of component b) by a polylactatediol. These polylactatediols have the advantage that on hydrolysis, for example in gastric fluid, they form toxicologically acceptable monomers.

The amounts of component b) in the polyurethane according to the invention are in the range from 20 to 45% by weight, preferably in the range from 22 to 40% by weight, particularly preferably in the range from 23 to 35% by weight.

The other component c) comprises compounds which have at least two amino groups able to react with isocyanate groups and, in addition, ionic groups or potentially ionic groups which can be converted by a simple neutralization or quaternization reaction into ionic groups. Introduction of monomers c) makes the polyurethanes self-dispersible, ie. in this case no dispersing auxiliaries such as protective colloids or emulsifiers are required on dispersion in water.

The introduction of cationic or anionic groups can take place by also using diamines having (potentially) cationic or (potentially) anionic groups.

However, the ionic groups are preferably introduced by also using comparatively low molecular weight compounds, in particular diamines with a molecular weight below 500 g/mol, having (potentially) ionic groups.

Preferred (potentially) ionic components c) are N-alkyldialkanolamines such as N-methyldiethanolamine, N-ethyldiethanolamine, diamino sulfonates such as the Na salts of N-(2-aminoethyl)-2-aminoethanesulfonic acid, diamino carboxylic acids or carboxylates such as lysine or the Na salt of N-(2-aminoethyl)-2-aminoethanecarboxylic acid and diamines having at least one additiional tertiary amine nitrogen, e.g. N-methyl-bis(3-aminopropyl)amine.

Particular preference is given to sulfo-containing diamines and their salts such as N-(2-aminoethyl)-2-aminoethanesulfonic acid and its Na, K or ammonium salts.

Conversion of the potentially ionic groups, which may initially be incorporated into the polyadduct, into at least partially ionic groups takes place in a conventional way by neutralization of the potentially anionic or cationic groups or by quaternization of tertiary amine nitrogen atoms.

Employed for the neutralization of potentially anionic groups, e.g. carboxyl groups or, preferably, sulfonate groups, are inorganic and/or organic bases such as alkali metal hydroxides, carbonates or bicarbonates, ammonia or primary, secondary and, with particular preference, tertiary amines such as triethylamine or dimethylaminopropanol.

Suitable for converting the potentially cationic groups, e.g. the tertiary amine groups, into the corresponding cations, e.g. ammonium groups, are, as neutralizing agents, inorganic or organic acids, e.g. hydrochloric, phosphoric, formic, acetic, fumaric, maleic, lactic, tartaric or oxalic acid or, as quaternizing agents, for example methyl chloride, methyl bromide, methyl iodide, dimethyl sulfate, benzyl chloride, chloroacetates or bromoacetamide. Further neutralizing or quaternizing agents are described, for example, in U.S. Pat. No. 3,479,310 (Column 6).

This neutralization or quaternization of the potential ionic groups can take place before, during or, preferably, after the isocyanate polyaddition reaction.

The amounts of component c) in the polyurethane according to the invention are in the range from 10 to 45% by weight, preferably in the range from 15 to 43% by weight, particularly preferably in the range from 20 to 43% by weight.

Polyisocyanates (component d) which should be particularly mentioned are diisocyanates $X(NCO)_2$, where X is an aliphatic hydrocarbon radical having 4 to 12 carbon atoms, a cycloaliphatic or aromatic hydrocarbon radical having 6 to 15 carbon atoms or an araliphatic hydrocarbon radical having 7 to 15 carbon atoms. Examples of diisocyanates of these types are tetramethylene diisocyanate, hexamethylene diisocyanate, dodecamethylene diisocyanate, 1,4-diisocyanatocyclohexane, 1-isocyanato3,5,5-trimethyl-3-isocyanatomethylcyclohexane(isophorone diisocyanate), 2,2-di(4-isocyanatocyclohexyl)propane, trimethylhexane diisocyanate, 1,4-diisocyanatobenzene, 2,4-diisocyanatotoluene, 2,6-diisocyanatotoluene, di(4-isocyanatophenyl)methane, p-xylylene diisocyanate, m- or p-tetramethylxylylene diisocyanate, and mixtures consisting of these compounds. It is also possible to use small amounts of compounds with one or more than two isocyanate functionalities.

The diisocyanates which are preferably used are isophorone diisocyanate and hexamethylene diisocyanate.

It is also possible to replace up to 10 mol % of the abovementioned diisocyanate by polyisocyanates such as Basocyanat® HI 100 (supplied by BASF).

The amounts of component d) in the polyurethane according to the invention are in the range from 30 to 50% by weight, preferably in the range from 32 to 48% by weight, particularly preferably in the range from 32 to 45% by weight.

Further additives (component e) which may also be used are emulsifiers or protective colloids.

Examples of emulsifiers and protective colloids to be mentioned are alkali metal salts of long-chain fatty acids, alkyl sulfates and alkylsulfonates, alkylated arylsulfonates or alkylated oxydiphenylsulfonates.

Further suitable emulsifiers are products of the reaction of alkylene oxides, especially ethylene or propylene oxide, with fatty alcohols, fatty acids, phenol or alkylphenols.

Examples of protective colloids which can be used are polyvinyl alcohol, polyvinylpyrrolidone, methylcellulose, carboxymethylcellulose, hydroxypropylcellulose, hydroxypropylmethylcellulose, starch, gelatin, casein and the like.

The K values of the polymers should be in the range from 20 to 150, preferably 25 to 120, particularly preferably in the range from 30 to 80. The K value required in each case can be adjusted in a conventional way through the composition of the starting materials. The K values are measured by the method of Fikentscher, Cellulosechemie, 13 (1932) 58–64 and 71–74, at 25° C. in 0.1% by weight solution in N-methylpyrrolidone.

The acid number (or the corresponding salt number) of the polyurethane according to the invention is determined by the composition and the concentration of the compounds of component c). The acid number is from 30 to 120, in particular from 40 to 90.

The water-soluble or water-dispersible polyurethanes according to the invention are expediently prepared by reacting monomers a, b and d in the presence of an inert, water-miscible solvent to give polyurethane prepolymers.

Suitable organic solvents are in principle all aprotic organic solvents, especially those with a boiling point of from 40 to 90° C. under atmospheric pressure. Examples which may be mentioned here are tetrahydrofuran, ethyl acetate and, especially, methyl ethyl ketone and acetone.

The structural components of the polyurethanes are generally reacted in the abovementioned solvents at from 20 to 160° C., in particular from 40 to 90° C.

The reaction of the diisocyanates can be speeded up by also using conventional catalysts, e.g. dibutyltin dilaurate, tin(II) octoate or diazabicyclo[2.2.2]octane.

The solids content of the resulting organic solution before dispersion in water is normally from 20 to 90% by weight, in particular 50 to 80% by weight.

The organic solution of polyurethane prepolymers, ie. polyurethanes which still contain free isocyanate groups, is reacted with the amino-functional components c), in the presence or absence of water, to give the final product.

Conversion of potential salt groups, e.g. sulfo groups or tertiary amino groups, which have been introduced into the polyurethane via monomers c), into the corresponding ions takes place by neutralization with bases or acids or by quaternization of the tertiary amino groups before or during the dispersion of the polyurethanes in water.

The solids content of the resulting aqueous polyurethane dispersions or solutions is, as a rule, from 10 to 70% by weight, in particular 15 to 50% by weight.

The polyurethane dispersions or solutions can be converted by various drying processes such as spray drying, fluidized spray drying, drum drying or freeze drying into powder form, from which an aqueous dispersion or solution can be prepared again by redispersion in water.

The water-soluble or water-dispersible polyurethanes according to the invention are outstandingly suitable as film formers and/or binders which are soluble or dispersible in gastric fluid for pharmaceutical presentations.

The invention therefore also relates to solid pharmaceutical presentations having a coating or binder consisting of a) 0.1–30% by weight of at least one polyol, b) 20–45% by weight of at least one polyetherpolyol, c) 10–45% by weight of at least one diamine comprising an ionic group, d) 30–50% by weight of at least one polyisocyanate with or without e) further additives, where components a) to e) may have the meanings mentioned above.

The coated presentations are preferably inter alia film-coated tablets, film-coated microtablets, sugar-coated tablets, coated pastilles, capsules, crystals, granules or pellets.

The binder-containing presentations are preferably inter alia tablets, microtablets, cores, granules or pellets.

As shown in Table 1, the aqueous solutions of the polyurethanes according to the invention have a distinctly lower viscosity than corresponding solutions of hydroxypropylmethylcellulose.

TABLE 1

|  | Viscosity (30% by weight aq. solution) [mPas] | Viscosity (20% by weight aq. solution) [mPas] |
| --- | --- | --- |
| Polyurethane A [1] | 8 | — |
| Polyurethane B [2] | 40 | — |
| Polyurethane C [3] | 21 | — |
| Pharmacoat ® 606 | — | >2000 |

Composition (% by weight):
[1] 31.35% poly THF (MW 650), 0.71% 1,6-hexanediol, 40.21% isophorone diisocyanate, 27.73% sodium N-(2-aminoethyl)-2-aminoethanesulfonate
[2] 23.15% poly THF (MW 650), 0.95% 1,6-hexanediol, 33.60% isophorone diisocyanate, 42.30% sodium N-(2-aminoethyl)-2-aminoethanesulfonate
[3] 29.46% poly THF (MW 650), 1.48% 1,4-cyclohexanedimethanol, 41.56% isophorone diisocyanate, 27.5% sodium N-(2-aminoethyl)-2-aminoethanesulfonate It is thus possible to employ more concentrated polymer formulations when coating tablets with the polyurethane dispersions as well as for binder applications, which means that the processes can be made considerably less costly and less time-consuming.

Redispersion of the powdered or granular polyurethanes to give aqueous dispersions or solutions takes place considerably faster than with other film formers or binders, because the polyurethanes are thoroughly wetted with water, form few aggregates and dissolve very rapidly. Aqueous dispersions of the polyurethanes according to the invention are extremely resistant to shearing and far exceed commercially available pharmaceutical dispersions such as acrylate/methacrylate dispersions.

Tablets soluble in gastric fluid which are coated with the polyurethanes according to the invention show a disintegration time which is only slightly prolonged by comparison with the core, i.e. the film coating dissolves very rapidly in simulated gastric fluid.

In the case of hydroxypropylmethylcellulose in the form of Pharmacoat 606 as coating material, disintegration takes distinctly longer (see Examples 2, 3 and Comparative Example). In addition, the use according to the invention of the polyurethanes increases the mechanical strength of the tablets very much more than does hydroxypropylmethylcellulose.

The extent of tablet swelling depends on the ancillary substances and active ingredients used, and on the storage times and conditions, such as temperature and humidity. A rigid film coating is subject to fissuring when the core swells. This is why the elasticity of film formers is an important variable. Polyurethanes have exceptional flexibility and elasticity. Thus, the ultimate elongation may be up to 300%. Fissuring is therefore not to be expected even with severe swelling of the core.

The polyurethanes can be applied in pure form or else together with conventional ancillary substances to the core containing active ingredient. Examples of conventional ancillary substances are colored pigments for coloring, white pigments such as titanium dioxide to increase the covering power, talc and silica as antistick agents, polyethylene glycols, glycerol, propylene glycol, triacetin, triethyl citrate as plasticizer and various surface-active substances such as sodium lauryl sulfate, polysorbate 80, Pluronics and Cremophors, to improve the wetting characteristics. The substances mentioned as examples do not represent a limitation. It is possible to use all additives known to be suitable for film coatings soluble in gastric fluid.

It is furthermore possible to combine the polyurethanes with other film formers or polymers in the ratio from 1:9 to 9:1.

Examples of polymers which can be employed for this purpose are the following:

Polyvinylpyrrolidone, polyvinylpyrrolidone copolymers, water-soluble cellulose derivatives such as hydroxypropylcellulose, hydroxypropylmethylcellulose, methylcellulose, hydroxyethylcellulose, acrylate and methacrylate copolymers, polyethylene glycols, polyethylene oxide/polypropylene oxide block copolymers.

The coating processes which can be used are the conventional processes such as coating in a fluidized bed or a horizontal drum coater, and dip-coating and pan-coating processes. Besides the tablet application, the polymers according to the invention can also be employed for coating other pharmaceutical formulations such as granules, pellets, crystals or capsules. The novel coatings are applied in the conventional thickness of 5–200 μm, preferably 10–100 μm.

When used as binders, a distinction is made between wet and dry binders depending on the method of processing. The latter are used inter alia in direct tabletting and in dry granulation or compaction. In these cases, the binder is mixed with the active ingredient, with or without other ancillary substances, and then subjected to direct tabletting, or granulation or compaction.

Wet granulation contrasts with this in that the active ingredient/ancillary substance mixture is moistened with a solution of the binder in water or an organic solvent, and the moist composition is forced through a screen and then dried. The moistening and drying can moreover take place in parallel, as, for example, in fluidized bed granulation.

For optimal processing, the binder should give low-viscosity solutions because viscous solutions result in inhomogeneous granules.

A binder is intended to result in uniform, hard, abrasion-resistant granules or tablets. Fracture resistance is particularly important for tablets because many active ingredients are difficult to compress and thus afford tablets with inadequate mechanical strength.

In addition, the disintegration of the drug forms, and the rate of release of the active ingredients should experience negligible adverse effects from the binder.

Examples of the most commonly used binders are polyvinylpyrrolidone, vinyl acetate/vinylpyrrolidone copolymers, gelatin, starch paste, maltodextrins, hydroxyalkylated and carboxyalkylated cellulose derivatives such as hydroxypropylmethylcellulose, methylcellulose, sodium carboxymethylcellulose, and types of natural gums such as gum arabic, pectin or alginate.

Many of these binders have a high viscosity in solution and are difficult to process. The high viscosity means that the powder particles to be granulated are wetted poorly and inhomogeneously so that the result is inadequate granule strength and an unfavorable particle size distribution.

Many binders are moreover hygroscopic and swell when water is absorbed. This may result in drastic alterations in the properties of granules and tablets.

It has now been found, surprisingly, that the polyurethanes according to the invention have excellent binding effects and moreover have a negligible effect on disintegration at concentrations in the range from 0.5 to 20% by weight, preferably 1 to 10% by weight, of the complete formulation. Because of the good wetting characteristics of the polyurethanes it is moreover possible for the release of active ingredients of low solubility to be improved.

When the polyurethanes are used as binders, the resulting granules and tablets have exceptional mechanical strength and are stable even over long storage periods.

The preparation and use of the polyurethanes according to the invention is explained in detail in the following examples.

EXAMPLE 1

Preparation of the aqueous polyurethane dispersion [polyurethane D with the following compositon (% by weight): 31.84% poly THF (MW 650), 1.95% 1,6-hexanediol, 2.38% 1,4-cyclohexanedimethanol, 41.60% isophorone diisocyanate, 22.58% sodium N-(2-aminoethyl)-2-aminoethanesulfonate].

1.2 mol of polytetrahydrofuran (MW 650 g/mol), 0.4 mol of 1,6-hexanediol and 0.4 mol of 1,4-cyclohexanedimethanol were dissolved in methyl ethyl ketone (about 70% by weight solution) while stirring and heating to 50° C. in a four-neck flask equipped with stirrer, dropping funnel, thermometer, reflux condenser and a device for operating under nitrogen. Then, while stirring, 4.5 mol of isophorone diisocyanate were added dropwise, during which the temperature of the mixture rose. The mixture was stirred under reflux until the NCO content remained virtually constant. The mixture was cooled and diluted with acetone to give an approximately 50% by weight solution. Then 2.5 mol of sodium N-(2-aminoethyl)-2-aminoethanesulfonate (50% by weight aqueous solution) were stirred in at <30° C. Stirring was continued at 50° C. for 30 minutes. Then water was added and the organic solvent was removed by distillation under reduced pressure, after addition of one drop of silicone antifoam, at about 40° C. A stable dispersion of the polyurethane was obtained. The product had a K value of 60.

EXAMPLE 2

Preparation of Propranolol HCl Film-coated Tablets (Coating Soluble in Gastric Fluid)

9 mm biconvex tablet cores containing 40 mg of propranolol HCl (supplied by Knoll AG), 195.0 mg of Ludipress® (supplied by BASF AG), 12.50 mg of Kollidon® VA 64 (supplied by BASF AG) and 2.50 mg of magnesium stearate were provided in a horizontal drum coater (Manesty 24" Accela-Cota) with a film coating of the following composition:

| | |
|---|---|
| Polyurethane A | 10.0% by weight |
| Lutrol ® E 6000 (BASF AG) | 1.0% by weight |
| Sicovit ® red (BASF AG) | 1.5% by weight |
| Titanium dioxide BN 56 (Kronos) | 3.0% by weight |
| Powdered talc (Riedel de Haen) | 4.5% by weight |
| Water | 80.0% by weight |

The spray dispersion was prepared by dissolving the polyurethane A and Lutrol® E 6000 in water, adding Sicovit® red, titanium dioxide and talc and then homogenizing in a corundum disk mill. 1260 g (including an overage of 10% for spray losses) were applied at a rate of 30 g/min to 5000 g of cores using a nozzle with a width of 1.0 mm under a pressure of 2.0 bar with an inlet air temperature of 60° C. The spraying was followed by drying at 60° C. for 5 min.

The resulting red film-coated tablets were smooth and slightly glossy and had the following properties:

| | |
|---|---|
| Appearance: | smooth surface, clear imprint |
| Disintegration (simulated gastric fluid): | 6 min. 44 s. |
| Disintegration time difference (Coated tablet - core): | 1 min. 15 s. |
| Fracture resistance: | 115 N |
| Fracture resistance difference (Coated tablet - core): | 46 N |

Comparative Example

Pharmacoat® 606 (hydroxypropylmethylcellulose from Shin-etsu) was employed in place of polyurethane A in the process of Example 2.

The resulting tablets had the following properties:

| | |
|---|---|
| Appearance: | slightly rough surface, clear imprint |
| Disintegration (simulated gastric fluid): | 1 min. 12 s. |

-continued

| | |
|---|---|
| Disintegration time difference (Coated tablet - core): | 6 min. 43 s. |
| Fracture resistance: | 87 N |
| Fracture resistance difference (Coated tablet - core): | 18 N |

EXAMPLE 3

Polyurethane E [with the following composition (% by weight): 28.7% poly THF (MW 1000), 6.8% 1,6-hexanediol, 42.0% isophorone diisocyanate, 22.50% sodium N-(2-aminoethyl)-2-aminoethanesulfonate] was processed as in Example 2. The spray solution used had the following composition:

| | |
|---|---|
| Polyurethane E | 20.0% by weight |
| Lutrol ® E 6000 (BASF AG) | 1.0% by weight |
| Sicovit ® red (BASF AG) | 1.5% by weight |
| Titanium dioxide BN 56 (Kronos) | 3.0% by weight |
| Powdered talc (Riedel de Haen) | 4.5% by weight |
| Water | 70.0% by weight |

Once again, smooth, slightly glossy, red film-coated tablets were obtained.

| | |
|---|---|
| Appearance: | smooth surface, clear imprint |
| Disintegration (simulated gastric fluid): | 6 min. 55 s. |
| Disintegration time difference (Coated tablet - core): | 1 min. 26 s. |
| Fracture resistance: | 119 N |
| Fracture resistance difference (Coated tablet - core): | 50 N |

EXAMPLE 4
Use as Binder in Glibenclamide Tablets 910 g of calcium hydrogen phosphate (from Rhone Poulenc) and 10 g of glibenclamide (Arzneimittelwerk Dresden) were passed through a 0.8 mm screen and mixed in a Turbula mixer (from Bachofen) for 5 min. This powder mixture was slowly moistened while stirring in a Stephan mixer (from Stephan) with 110 g of a 27% by weight aqueous formulation of polyurethane A. To complete the moistening after addition of the binder formulation, stirring was continued at 800 rpm for 2 min. The moist composition was then passed through a 0.8 mm screen and dried on a tray at 25° C. for 20 h. Addition of 45 g of Kollidon® CL (from BASF) and 5 g of magnesium stearate (from Bärlocher) was followed by final mixing once again in a Turbula mixer for 5 min. This tabletting mixture was then compressed to biplanar, beveled tablets with a diameter of 12 mm and a total weight of 500 mg in a Korsch PH 106 rotary press (from Korsch) with a force of 10 kN and 18 kN.

| Properties: | 10 kN force | 18 kN force |
|---|---|---|
| Fracture resistance: | 31 N | 66 N |
| Friability: | 0.19% | 0.13% |
| Disintegration: | <15 s. | <15 s. |

Comparative Example

Production took place as in Example 4 but with hydroxypropylmethylcellulose (Pharmacoat® 603, from Shin-etsu) as binder, it being necessary to reduce the concentration of the binder in the solution to 20% by weight for reasons of viscosity.

| Properties: | 10 kN force | 18 kN force |
|---|---|---|
| Fracture resistance: | 18 N | 45 N |
| Friability: | 6.3% | 0.27% |
| Disintegration: | 25 s. | 35 s. |

EXAMPLE 5
Use as Binder in a Hydrochlorothiazide Tablet

A mixture of 8950 g of fine Lactose (from Meggle), 350 g of hydrochlorothiazide (from Chemag) and 350 g of Kollidon® CL (from BASF) is sprayed with a binder formulation consisting of 350 g of polyurethane E and 3000 g of water in a WSG 15 fluidized bed granulating apparatus (from Glatt) and, in this way, granulated in the fluidized bed.

The following process parameters were set:

| | |
|---|---|
| Inlet air temperature: | 90° C. |
| Outlet air temperature: | 37° C. |
| Spraying rate | 143 g/min |
| Spraying pressure | 4 bar |

The granulation was followed by drying in the apparatus at 90° C. for 2.5 min. The granules were passed through a 0.8 mm screen and mixed with 5 g of magnesium stearate (from Bärlocher) in a Turbula mixer (from Bachofen) for 5 min. A Korsch PH 106 (from Korsch) rotary press was used to produce biplanar, bevelled tablets with a diameter of 10 mm and a total weight of 300 mg at a force of 18 kN.

Granule properties:

| | |
|---|---|
| Angle of repose: | 30° |
| Appearance: | very uniform, with negligible fines |
| Tablet properties: | |
| Fracture resistance: | 220 N |
| Friability: | <0.1% |
| Disintegration: | 4 min. 10 s. |
| Release in simulated gastric fluid (Ph. Eur.) | 91% after 15 min. |

Comparative Example

Production took place as in Example 5 but with hydroxypropylmethylcellulose (Pharmacoat® 603, from Shin-etsu) as binder.

Granule properties:

| Angle of repose: | 33° |
|---|---|
| Appearance: | somewhat inhomogeneous, some larger lumps |

Tablet properties:

| Fracture resistance: | 175N |
|---|---|
| Friability: | 0.2% |
| Disintegration: | 5 min. 10 s. |
| Release in simulated gastric fluid (Ph. Eur.) | 82% after 15 min. |

We claim:

1. A coating or binder for pharmaceutical preparations, said coating or binding comprising a water-soluble or water-dispersible polyurethane consisting of
   a) 0.1–30% by weight of at least one polyol,
   b) 20–45% by weight of at least one polyetherpolyol
   c) 10–45% by weight of at least one diamine comprising an ionic group,
   d) 30–50% by weight of at least one polyisocyanate with or without
   e) further additives.

2. The coating or binder composition of claim 1 wherein the polyol is a diol having from 2 to 10 carbon atoms.

3. The coating or binder composition of claim 1 wherein the polyetherpolyol is a polytetrahydorfuran having a molecular weight of from 300 to 6000 g/mol.

4. The coating or binder composition of claim 1, wherein at least one $SO_3$ group is attached to the diamine.

5. The coating or binder composition of claim 1 wherein the polyisocynate is a diisocynate of formula $X(NCO)_2$, where X is selected from the group consisting of an aliphatic hydrocarbon radical having from 4 to 12 carbon atoms, a cycloaliphatic or aromatic hydrocarbon radical having from 6 to 15 carbon atoms, and an araliphatic hydrocarbon radical having from 7 to 15 carbon atoms.

6. The coating or binder composition of claim 1 which has a K value of from 20 to 150.

7. A solid pharmaceutical presentation having a coating consisting of
   a) 0.1–30% by weight of at least one polyol,
   b) 20–45% by weight of at least one polyetherpolyol,
   c) 10–45% by weight of at least one diamine comprising an ionic group,
   d) 30–50% by weight of at least one polyisocyanate with or without
   e) further additives.

8. A solid pharmaceutical presentation as claimed in claim 7, which comprises the coating, besides other conventional ancillary substances, in a thickness of from 5 to 200 μm.

9. A solid pharmaceutical presentation as claimed in claim 1, wherein the coating is soluble in gastric fluid or dispersible in gastric fluid.

10. A solid pharmaceutical presentation having a binder consisting of
    a) 0.1–30% by weight of at least one polyol,
    b) 20–45% by weight of at least one polyetherpolyol,
    c) 10–45% by weight of at least one diamine comprising an ionic group,
    d) 30–50% by weight of at least one polyisocyanate with or without
    e) further additives.

11. A solid pharmaceutical presentation as claimed in claim 10, which comprises the binder in a concentration of from 0.5 to 20% by weight.

* * * * *